United States Patent
Goldstein et al.

(10) Patent No.: US 9,421,217 B2
(45) Date of Patent: Aug. 23, 2016

(54) SWEET TASTE RECEPTOR ANTAGONIST COMPOSITIONS

(71) Applicant: Four LLC, New York, NY (US)

(72) Inventors: Robert L. Goldstein, New York, NY (US); Grant Dubois, Roswell, GA (US); Arianne Perry, New York, NY (US)

(73) Assignee: Four LLC, New York, NY (US)

( * ) Notice: Subject to any disclaimer, the term of this patent is extended or adjusted under 35 U.S.C. 154(b) by 0 days.

(21) Appl. No.: 14/738,326

(22) Filed: Jun. 12, 2015

(65) Prior Publication Data
US 2015/0359809 A1    Dec. 17, 2015

Related U.S. Application Data

(60) Provisional application No. 62/025,725, filed on Jul. 17, 2014, provisional application No. 62/011,096, filed on Jun. 12, 2014.

(51) Int. Cl.

| | |
|---|---|
| *A61K 8/27* | (2006.01) |
| *A61K 8/368* | (2006.01) |
| *A61K 31/704* | (2006.01) |
| *A61K 9/00* | (2006.01) |
| *A61K 8/58* | (2006.01) |
| *A61K 8/60* | (2006.01) |
| *A61K 31/315* | (2006.01) |
| *A61K 33/24* | (2006.01) |
| *A61K 38/16* | (2006.01) |
| *A61K 45/06* | (2006.01) |
| *A61Q 11/00* | (2006.01) |
| *A23L 1/30* | (2006.01) |
| *A23L 1/304* | (2006.01) |
| *A23L 3/20* | (2006.01) |
| *A23G 3/36* | (2006.01) |
| *A23G 3/38* | (2006.01) |
| *A23G 3/48* | (2006.01) |
| *A23L 1/22* | (2006.01) |

(52) U.S. Cl.
CPC .............. *A61K 31/704* (2013.01); *A23G 3/362* (2013.01); *A23G 3/38* (2013.01); *A23G 3/48* (2013.01); *A23L 1/22083* (2013.01); *A23L 1/3002* (2013.01); *A23L 1/3045* (2013.01); *A23L 3/205* (2013.01); *A61K 8/27* (2013.01); *A61K 8/368* (2013.01); *A61K 8/58* (2013.01); *A61K 8/602* (2013.01); *A61K 9/0056* (2013.01); *A61K 31/315* (2013.01); *A61K 33/24* (2013.01); *A61K 38/168* (2013.01); *A61K 45/06* (2013.01); *A61Q 11/00* (2013.01); *A23V 2002/00* (2013.01)

(58) Field of Classification Search
CPC .................... A61K 8/27; A61K 8/368
See application file for complete search history.

(56) References Cited

U.S. PATENT DOCUMENTS

| | | | |
|---|---|---|---|
| 6,746,695 B1 * | 6/2004 | Martin ................. | A61K 36/185 210/656 |
| 7,273,607 B2 * | 9/2007 | Schakel .................... | A23L 1/30 424/520 |
| 7,851,005 B2 * | 12/2010 | Bingley ............... | A23L 1/22008 424/49 |
| 2002/0136782 A1 * | 9/2002 | Fleischner ........... | A61K 31/137 424/725 |
| 2003/0133992 A1 * | 7/2003 | Bagchi ................... | A61L 31/05 424/643 |
| 2005/0276839 A1 | 12/2005 | Rifkin | |
| 2006/0286203 A1 * | 12/2006 | Boghani .................. | A23G 4/06 426/5 |
| 2008/0241281 A1 * | 10/2008 | Vediyappan ........... | A01N 37/46 514/1.1 |

FOREIGN PATENT DOCUMENTS

EP    2 243 473 A1    10/2010

OTHER PUBLICATIONS

International Search Report (PCT/ISA/210) issued in PCT Application No. PCT/US2015/035578 dated Jan. 4, 2016 (five (5) pages) "test".
Written Opinion (PCT/ISA/237) issued in PCT Application No. PCT/US2015/035578 dated Jan. 4, 2016 (six (6) pages).
P. M. Brala et al., "Effects of Sweetness Perception and Caloric Value of a Preload on Short Term Intake", Physiology & Behavior, vol. 30, 1983, XP25443939, pp. 1-9.
R. S. J. Keast, "The Effect of Zinc on Human Taste Perception", Journal of Food Science, vol. 68, No.5, 2003, XP2543961, pp. 1871-1877.

* cited by examiner

*Primary Examiner* — Benjamin Packard
(74) *Attorney, Agent, or Firm* — Dechert LLP

(57) ABSTRACT

The present disclosure relates to compositions comprising gymnemic acid, together with a form of zinc to block the unpleasant bitter taste of gymnemic acid as well as to extend the sweet taste blocking properties of gymnemic acid, resulting in palatable compositions for delivery to the oral cavity to block sweet taste receptors located therein. The present disclosure also relates to methods of reducing sugar consumption and reducing calorie intake via administration of such compositions to a subject.

22 Claims, No Drawings

SWEET TASTE RECEPTOR ANTAGONIST COMPOSITIONS

PRIORITY DATA

This application claims priority, pursuant to 35 U.S.C. §119(e), to U.S. Provisional Patent Application Ser. No. 62/011,096, filed Jun. 12, 2014, and U.S. Provisional Patent Application Ser. No. 62/025,725, filed Jul. 17, 2014, both of which are incorporated herein by reference in their entireties.

FIELD OF THE INVENTION

The present disclosure relates to compositions comprising gymnemic acid, together with a form of zinc to block the unpleasant bitter taste of gymnemic acid as well as to extend the sweet taste blocking properties of gymnemic acid, resulting in palatable compositions for delivery to the oral cavity to block sweet taste receptors located therein. The present disclosure also relates to methods of reducing sugar consumption and reducing calorie intake via administration of such compositions to a subject.

BACKGROUND OF THE INVENTION

Gymnemic acid is extracted from *Gymnema sylvestre*, a woody climbing plant native to India, Africa, and China. Gymnemic acid is a dietary supplement sold worldwide, primarily in encapsulated forms. (See Ogawa et al., *J. Food Hygienic Soc Japan* (2004) 45:8-18) Gymnemic acid is known to temporarily block the sensation of sweet taste when applied directly to the oral cavity. (See Kurihara, 1969 and Sanematsu, *J. Biol. Chem.* (2014) 289:25711-25720). Studies have shown that subjects given gymnemic acid consume fewer calories than subjects given a placebo (See Brala et al., *Physiol. Behav.* (1983) 30:1-9). However, gymnemic acid is known to have an intense bitter taste that is unpalatable to humans. (See, for example, U.S. Publication No. 2004/007180).

Traditionally, in the field of flavor science, one would add a sweetener such as sucrose to a composition to mask the bitter taste of an essential ingredient. Intensely bitter ingredients would require larger amounts of sucrose or perhaps a more intense artificial sweetener such as sucralose to mask the bitterness. However, these traditional bitter blocking methods do not work to reduce the bitter taste of gymnemic acid, as a result of gymnemic acid's sweet taste blocking property. Moreover, the use of an intense natural or artificial sweetener can interfere with the desired sweet blocking activity of the gymnemic acid, as both sweeteners and gymnemic acid interact and bind with sweet taste receptors (Sanematsu, *J. Biol. Chem.* (2014) 289:25711-25720).

It is also common in the field of flavor science, when working with a composition containing a bitter ingredient, to prepare an encapsulated or tablet dosage form that is intended to be immediately swallowed. This approach avoids any bitterness problem because the bitter ingredient never directly contacts the oral cavity. However, such a dosage form is not feasible for a composition containing gymnemic acid, which is intended to directly contact the oral cavity and tongue, and then be swallowed.

For more than a decade, attempts have been made to develop a diet product that delivers *Gymnema* directly into the oral cavity. However, due to the inability of known flavor science to effectively eliminate the intense bitterness of *Gymnema*, these attempts have failed. One such attempt is discussed in U.S. Publication No. 2004/007180 which describes a lozenge combining *Gymnema* leaf extract with a de-bittering agent, disclosing the bitter masking agent as "Comax Flavors #2588E17379." Sugarest™ gum, manufactured by Genotec Nutritionals, Inc. was marketed to temporarily block sweet taste receptors for 20-3( ) minutes. (Press Release, MM2 Group, Inc., MM2 Group's Sugarest™ Featured on TV News in Philadelphia (Apr. 12, 2007) available at PM Newswire's website. The product failed and has not been available for many years.

Supresalin is a composition containing gymnemic acids alleging to reduce sugar cravings for approximately 30 minutes. (http://supresalin.com/faqs/). Sugar Suppress 60 is another product containing gymnemic acids that claims to reduce calorie consumption and promote weight loss. However, this product is intensely bitter and unpalatable. After many failed attempts, there remains a need for a palatable, non-bitter composition of gymnemic acid, in a lingual delivery form, that fully blocks sweet taste for an extended period of time.

SUMMARY OF THE INVENTION

Described herein is a composition comprising gymnemic acid, together with a form of zinc to block the unpleasant bitter taste of gymnemic acid as well as to extend the sweet taste blocking properties of gymnemic acid, resulting in palatable compositions intended to directly contact the oral cavity to block sweet taste receptors located therein. As the sweet taste blockade effect of gymnemic acid requires the agent to remain in the oral cavity, there is a need for an effective means to reduce the bitter unpalatable taste of gymnemic acid during its delivery to the oral cavity. This need is met by the lingual delivery forms, compositions, and methodologies of the present disclosure, which preferably allow for delivery of gymnemic acid to the oral cavity together with a form of zinc, blocking the bitter taste of gymnemic acid.

In general and according to certain embodiments, the lingual delivery forms and compositions of the present disclosure deliver gymnemic acid, together with a form of zinc, to the sweet taste receptors of the tongue, resulting in exceptional durations of sweetness blockade while simultaneously reducing or eliminating its bitter taste during application.

The present invention may be directed to a lingual delivery form comprising gymnemic acid and at least one form of zinc. The lingual delivery may include, but is not limited to, a lozenge, an orally disintegrating tablet, an orally dispersible tablet, a troche, a hard candy, a soft candy, a jelly, a gum, an edible film, an orally dissolvable film, a wafer, a drop, an oral spray, a liquid, a powder and combinations thereof. The disintegration time of the orally disintegrating tablet may be in the range of from about 30 seconds to about 5 minutes.

The form of zinc may include, but is not limited to, zinc acetate, zinc carbonate, zinc chloride, zinc citrate, zinc gluconate, zinc sulfate, zinc hydrosulfite, zinc bisulfite, zinc oxide, zinc halide, zinc hydride, zinc carbide, and combinations thereof. Preferably, the form of zinc is a GRAS (Generally Recognized as Safe, fda.gov/Food/IngredientsPackagingLabeling/GRAS/) approved zinc salt, most preferably zinc gluconate.

The gymnemic acid may be present as an inorganic salt of gymnemic acid, an organic salt of gymnemic acid, a cyclodextrin complex of gymnemic acid, a cryptand complex of gymnemic acid, a hydrate of gymnemic acid, a solvate of gymnemic acid, and combinations thereof. The solvate of gymnemic acid may include ethanol solvates of gymnemic acid.

The lingual delivery form may further comprise mint.

The lingual delivery form may further comprise a bitter taste inhibitor. The bitter taste inhibitor may include, but is not limited to, sodium salt, a lipoprotein, and combinations thereof.

The lingual delivery form may further comprise at least one sour taste inhibitor. The sour taste inhibitor may be miraculin.

The present inventor provides methods of using the present lingual delivery forms and compositions. The present invention provides a method of reducing sugar consumption, comprising administering the composition and lingual delivery forms of the present invention to a subject. Moreover, the present invention provides a method of reducing calorie intake, comprising administering the composition and lingual delivery forms to a subject, as well as a method of reducing dental caries, comprising administering the composition and lingual delivery forms to a subject.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

It must also be noted that ratios, concentrations, amounts, and other numerical data may be expressed herein in a range of formats. It is to be understood that such a range of formats is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

As used herein, the phrase "sweetness blockade" is defined as the attenuation of the perceptible sweetness of a food or beverage or other substance introduced into the oral cavity. Sweetness blockade and sweet taste block are synonymous.

As used herein, the phrase "reduced bitter taste" is defined as the reduction of the bitter taste associated with a compound (e.g., gymnemic acid). In certain embodiments, the reduced bitter taste is a reduction of about 50% or more, about 75% or more, about 85% or more, about 90% or more, about 95% or more, or about 99% or more. As used herein, the phrase "eliminate bitter taste" is defined as the reduction of the bitter taste associated with a compound (e.g., gymnemic acid) by about 100%.

Gymnemic acid is not selective in its sweetness blockade. Therefore, any food or drink or other substance containing sweet tastants which is ingested or introduced into the oral cavity during the period following delivery of gymnemic acid to the oral cavity do not taste sweet or their sweet flavor is markedly diminished. Moreover, the presence of any bitter or sour flavors in such food or drink is perceived as being amplified since bitter and sour flavors are no longer masked by the sweet flavors. Use of gymnemic acid through delivery to the oral cavity, including the tongue, stops cravings for sweet tastants in food or drink, resulting in a decreased consumption of such high-calorie foods. The link between sweetness perception and choice of sweet foods for consumption is known. (See Brala et al., *Physiol. Behav.* (1983) 30:1-9).

A drawback to using gymnemic acid in this manner is that gymnemic acid is known to have an unpleasant and intense bitter taste that is unpalatable to humans. Another drawback is that while gymnemic acid blocks the sensation of sweet taste, such effect is transitory and lasts for only a short period of time. Thus, there exists a continuing need for improved gymnemic acid-based compositions that can block the sensation of sweet taste for longer periods of time while reducing or eliminating the bitter taste of the gymnemic acid. Moreover, there exists a need for an effective means to greatly reduce or eliminate the intense bitter and unpalatable taste of gymnemic acid during its delivery to the oral cavity.

Much is known about sweet taste receptors. Sweetness is one of the five primary categories of taste sensed by humans. Receptors initiating this sensation are located in one of three kinds of taste bud cells known as Type I, Type II, and Type III, which are located in taste buds located primarily on the tongue, but are also found on the soft palate and other regions of the oral cavity. Sweet taste receptors are located in different subsets of Type II taste bud cells. Sweetness sensing taste bud cells express a single heterodimeric receptor identified as T1R2/T1R3.

In contrast, bitter taste transduction mechanisms are complex and not fully understood. It is known that human bitter taste is initiated by activation of 26 T2R receptors which are generally accepted to exist as a mixture of homo-dimeric and hetero-dimeric species in bitter-sensitive taste bud cells, thus providing a total of 346 possible functional receptors, where the relative numbers of these dimeric species are thought to vary from person to person. (See C. Kuhn et al., *Chem. Senses* 2010, 35:395-406). Such diversity between people demonstrates the complexity of bitter taste in contrast to other tastes such as sweet and sour. Furthermore, given that gymnemic acid is a complex mixture of over 20 unique triterpenoid saponins (see Imoto et al., *J Chromatography* (1991) 557: 383-389), which all may have different bitter taste attributes, blocking the bitter taste of gymnemic acid presents a significant challenge.

Given that there 26 T2R bitter receptors responsible for sensing bitter stimuli, blocking the associated bitterness is very difficult when multiple receptors are activated. The bitter response created by a complex mixture of molecules contained in an herbal extract, such as a composition containing gymnemic acid, would be expected to trigger a large number of individual bitter receptors. It would thus be expected that a single agent with bitter blocking properties would not completely abolish the bitter taste of gymnemic acid.

It is known that zinc has some ability to block both sweet and bitter tastes. The utilization of zinc salts has been described in previous publications as a taste modifier. (Keast, *JFS* (2003) 68:1871-1877). While gymnemic acid inhibits the sweetness of all natural and artificial sweeteners, zinc salts are selective in their inhibition and are not universal inhibitors. For example, Keast and Breslin have demonstrated that zinc sulfate is an effective bitterness inhibitor against quinine, denatonium benzoate, and tetralone but has no significant bitterness inhibitory activity against sucrose octaacetate, pseudoephedrine, and dextromethorphan. (Keast, *JFS* (2003) 68:1871-1877) For further example, it has been observed that $ZnSO_4$ inhibits the bitterness of quinine hydrochloride (QHC1) by up to 70% (Keast, *JFS* (2003) 68:1871-1877). However it must be noted that zinc may only interfere with the mechanism(s) responsible for bitter taste transduction of a subset of bitter compounds, of which there are thousands, rather than all bitter compounds. (Keast, *JFS* (2003) 68:1871-1877).

Zinc alone is not anticipated to be fully effective as a taste-modifier, and is not sufficient to provide a palatable composition. To be completely effective, the zinc is traditionally accompanied by additional flavor masking agents such as sucrose, fructose, sorbitol, xylitol, artificial sweeteners and/or flavoring compositions (i.e., fruit or citrus flavors). Moreover, zinc itself is known to have a metallic, chalky, astringent objectionable aftertaste common to metallic ions, and an additional flavor masking agent is also needed to mask the unpleasant taste of the zinc. Thus, zinc is not considered to be a single agent that may be used to fully block a bitter tasting ingredient.

Nonetheless, it was surprisingly found that the addition of a form of zinc to a gymnemic acid extract not only results in a composition that does not require any further taste-masking agents to taste palatable and block sweet taste, but the duration of the sweetness blockage is extended to at least 60-80 minutes, greater than the duration of sweetness blockade obtains with gymnemic acid alone.

Through compositions of the present invention, it has been unexpectedly found that when gymnemic acid is combined with zinc, the bitter taste of the gymnemic acid is reduced and almost completely eliminated while the sweet taste blocking properties of the gymnemic acid remain effective. Moreover, it has been unexpectedly found that compositions of gymnemic acid together with a form of zinc block sweet taste in human subjects for a longer period of time than administration of gymnemic acid alone or zinc alone. It has been unexpectedly found that the length of the sweetness blockade may be extended to a duration of at least 60-80 minutes or longer upon the delivery to the oral cavity of compositions that contain a combination of gymnemic acid and a form of zinc, greater than the duration of sweetness blockade obtains with gymnemic acid alone.

The present invention provides delivery of gymnemic acid to the oral cavity in order to block the sensation of sweet tastants. Thus, during the ingestion of any sweet food or drink, the sweet tastant does not lead to the perception of sweet taste. The person or subject using the composition of the present invention will no longer be able to experience the sweet taste of what they are eating or drinking or introducing into the oral cavity, rendering most foods, drinks, and other substances unpalatable. Thus, the present invention provides a composition which allows the user to address their cravings for sweet foods immediately. Moreover, through more extended use, the user of the composition may modify their behavior because they no longer associate a pleasant feeling with foods that previously tasted sweet. Thus, the present invention also provides methods of to reduce sugar consumption and reduce calorie intake by a subject via administration to the subject of the gymnemic acid-containing compositions described herein.

In general and according to certain embodiments, the lingual delivery forms and compositions of the present disclosure deliver gymnemic acid to the sweet taste receptors of the tongue, resulting in exceptional durations of sweetness blockade while simultaneously reducing or eliminating gymnemic acid's bitter taste during application.

The unique and surprising performance of compositions containing both gymnemic acid and a form of zinc provides an advantage over prior art gymnemic acid formulations, providing longer periods of sweet taste blocking and allowing a subject to maintain the gymnemic acid-containing composition in the oral cavity for a longer duration without experiencing gymnemic acid's unpleasant bitter flavor.

Applicants surprisingly found that application of a composition comprising gymnemic acid together with a form of zinc as an additional sweetness inhibitor provided a total sweetness blockade greater than the sum of the sweetness blocking effects of zinc used individually, and gymnemic acid used individually. Synergy is defined as the cooperative action of discrete agencies such that the total effect is greater than the two or more effects taken independently.

Given the complexity of the human bitter taste receptor system with as many as 346 functional receptors, where it is commonly found that specific bitterants activate multiple bitter receptors and where there is as yet no knowledge of the specific bitterant receptors activated by gymnemic acid, the prediction of the identity of a specific bitterness inhibitor for gymnemic acid is not possible. Furthermore, forms of zinc are specific in their bitterness inhibitory activity and not broadly applicable. Thus, it would not be expected that a combination of a form of zinc and gymnemic acid would provide full sweet-taste blocking without any bitter taste, let alone provide a synergistic effect increasing the duration of the sweet taste blockade. Moreover, the loci of gymnemic acid and zinc binding to T1R2/T1R3 are not known. Without this knowledge, synergy cannot be predicted.

The "form of zinc" may be in any form, such as a zinc salt. For example, the zinc form may include, but is not limited to, forms of zinc generally recognized as safe by the U.S. FDA ("GRAS") such as zinc acetate, zinc carbonate zinc chloride, zinc gluconate, zinc hydrosulfite, zinc oxide and zinc sulfate, as well as zinc halide, zinc hydride, zinc carbide, zinc citrate, and zinc bisulfite, and as well as any combination thereof.

The lingual delivery forms and compositions of the present invention provide exceptional durations of sweetness blockade (e.g., about 30 minutes or more, about 60 minutes or more, about 80 minutes or more, about 90 minutes or more, or about 120 minutes or more), while simultaneously reducing or eliminating the bitter taste associated with gymnemic acid. It has been unexpectedly found that the length of the sweetness blockade may be extended to longer than gymnemic acid or zinc alone, for example to greater than 80 minutes, upon the delivery to the oral cavity of compositions including a combination of gymnemic acid and a form of zinc. Thus, the lingual delivery forms and compositions of the present invention have the ability to assist people in controlling their consumption of sweet foods and beverages that are high in calories.

One aspect of the present invention is a lingual delivery form comprising gymnemic acid and a form of zinc. As used herein, the term "lingual" refers to any area of the oral cavity containing taste receptors, including the tongue and any other location therein. The oral cavity can include the tongue, inside of the mouth, the buccal cavity, under the tongue, and the like. As used herein, the term "lingual delivery form" refers to any solid or liquid form or vehicle that can be used to deliver gymnemic acid, the at least one additional sweet taste inhibitor, and any other components, such as a bitter taste inhibitor or a sour taste inhibitor, to the taste receptors on the tongue as well as other taste receptors in the oral cavity of a subject.

Examples of such lingual delivery forms include, but are not limited to, lozenges, tablets, orally disintegrating tablets, orally dispersible tablets, troches, hard candies, soft candies, jellies, gums, edible films, orally dissolvable films, wafers, drops, oral sprays, liquids, and powders. In certain embodiments, the subject maintains a solid lingual delivery form comprising gymnemic acid and a form of zinc in the oral cavity for about 3 to 5 minutes. In other embodiments, the subject maintains a liquid lingual delivery form comprising gymnemic acid and a form of zinc in the oral cavity for about 3 to 5 minutes. In certain other embodiments, the lingual delivery form is an orally disintegrating tablet having a disintegration time in the range of from about 30 seconds to about 5 minutes. The disintegration time may be determined using the USP <2040> method for disintegration and dissolution of dietary supplements. The parameters for this method include deionized water, temperature of 35°-37° Celsius, and a sample size of greater than 6.

Another aspect of the present invention is a composition comprising gymnemic acid and a form of zinc which may also further comprise at least one additional sweet taste inhibitor, with the proviso that the at least one additional sweet taste inhibitor is not lactisole, sodium 3-(4-methoxyphenoxy) propionate, hodulcine, or ziziphin.

Yet another aspect of the present invention is a composition comprising gymnemic acid and a form of zinc, and at least one sour taste inhibitor The lingual delivery forms and the compositions of the present invention comprise gymnemic acid. As used herein, gymnemic acid refers to extracts of the plant *Gymnema sylvestre* which contain one or more triterpenoid saponins capable of inhibiting the sensation of sweet taste in a human. Also contemplated are compositions comprising gymnemic acid that include the synthetic counterparts of these extracted triterpenoid saponins. Examples of such compounds include, but are not limited to, compounds of Formula (I):

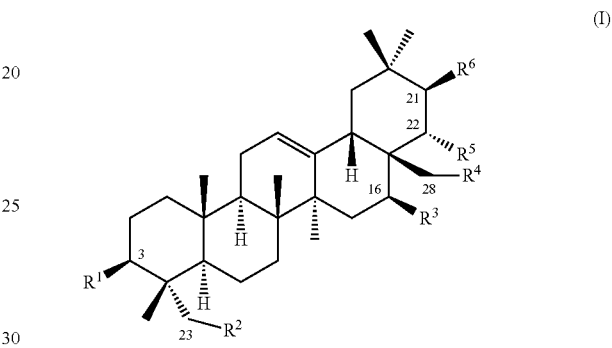

Wherein

| Entry | CAS # | $R^1$ (C-3) | $R^2$ (C-23) | $R^3$ (C-16) | $R^4$ (C-28) | $R^5$ (C-22) | $R^6$ (C-21) |
|---|---|---|---|---|---|---|---|
| 1 | 122168-40-5 | β-D-GlcA | OH | OH | Acetyl | OH | Tigloyl |
| 2 | 122144-48-3 | β-D-GlcA | OH | OH | Acetyl | OH | (S)-Methyl-butyloyl |
| 3 | 122074-65-1 | β-D-GlcA | OH | OH | OH | OH | (S)-Methyl-butyloyl |
| 4 | 121903-96-6 | β-D-GlcA | OH | OH | OH | OH | Tigloyl |
| 5 | 121903-99-9 | β-D-GlcA | OH | OH | OH | Tigloyl | Tigloyl |
| 6 | 121903-98-8 | β-D-Glc-(1→6)-β-D-GlcA | OH | OH | OH | OH | Tigloyl |
| 7 | 121903-97-7 | β-D-GlcA | OH | OH | OH | H | OH |
| 8 | 131653-19-5 | Structure A (see below) | OH | OH | OH | OH | (S)-Methyl-butyloyl |
| 9 | 131653-20-8 | Structure A (see below) | OH | OH | OH | OH | Tigloyl |
| 10 | 147934-05-2 | β-D-GlcA | OH | OH | Acetyl | OH | OH |
| 11 | 147899-35-2 | β-D-GlcA | OH | OH | Tigloyl | OH | Tigloyl |
| 12 | 147899-36-3 | b-D-Glc-(1→6)-b-D-GlcA | OH | OH | Acetyl | OH | Tigloyl |
| 13 | 155023-61-3 | β-D-GlcA | OH | OH | (S)-Methyl-butyloyl | OH | OH |
| 14 | 155023-62-4 | β-D-GlcA | OH | OH | Tigloyl | OH | OH |
| 15 | 154977-74-9 | β-D-GlcA | OH | OH | OH | Tigloyl | (S)-Methyl-butyloyl |
| 16 | 154977-75-0 | β-D-GlcA | OH | Tigloyl | OH | Tigloyl | OH |
| 17 | 154977-76-1 | β-D-GlcA | OH | OH | OH | OH | Benzoyl |

Structure A

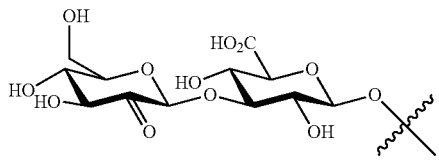

| Entry | CAS # | R¹ (C-3) | R² (C-23) | R³ (C-16) | R⁴ (C-28) | R⁵ (C-22) | R⁶ (C-21) |
|---|---|---|---|---|---|---|---|
| 18 | 154977-77-2 | β-D-GlcA | OH | OH | Benzoyl | OH | OH |
| 19 | 22467-07-8 | OH | OH | OH | OH | OH | OH |
| 20 | 121686-42-8 | β-D-GlcA | OH | OH | OH | OH | OH |
| 21 | 42483-24-9 | OH | OH | OH | OH | H | H |
| 22 | 62641-93-4 | Acetyl | Acetyl | Acetyl | Acetyl | H | H |
| 23 | 1581276-60-9 | OH | OH | OH | OH | OH | (S)-Methyl-butyloyl |
| 24 | 1581276-61-0 | OH | OH | OH | Acetyl | OH | (S)-Methyl-butyloyl |
| 25 | 1581276-62-1 | Acetyl | Acetyl | Acetyl | Acetyl | Acetyl | (S)-Methyl-butyloyl |
| 26 | 1581276-63-2 | OH | OH | OH | OH | OH | Tigloyl |
| 27 | 174324-52-8 | OH | OH | OH | OH | OH | H |
| 28 | 174324-49-3 | β-D-GlcA-(1→3)-β-D-Glc | OH | OH | OH | Tigloyl | H |
| 29 | 174324-48-2 | β-D-GlcA-(1→3)-β-D-Glc | OH | OH | OH | OH | H |

| Entry | CAS # | R¹ (C-3) | R² (C-23) | R³ (C-16) | R⁴ (C-28) | R⁵ (C-22) | R⁶ (C-21) |
|---|---|---|---|---|---|---|---|
| 30 | 174324-50-6 | β-D-GlcA | OH | OH | OH | Tigloyl | H |
| 31 | 174324-51-7 | β-D-GlcA | OH | OH | OH | OH | H |
| 32 | 175033-15-5 | β-D-GlcA | OH | OH | OH | Acetyl | Tigloyl |
| 33 | 174232-51-0 | β-D-GlcA | OH | Acetyl | OH | OH | Tigloyl |
| 34 | 199618-65-0 | β-D-GlcA | OH | OH | Acetyl | OH | Benzoyl |
| 35 | 199618-66-1 | OH | β-D-Xyl-(1→6)-β-D-Glc-(1→6)-β-D-Glc | OH | OH | H | OH |
| 36 | 199618-67-2 | OH | β-D-Xyl-(1→6)-β-D-Glc-(1→6)-β-D-Glc | OH | β-D-Glc-(1→6)-β-D-Glc | H | H |
| 37 | 199618-68-3 | OH | β-D-Xyl-(1→6)-β-D-Glc-(1→6)-β-D-Glc | OH | β-D-Glc-(1→6)-β-D-Glc | H | H |
| 38 | 133629-85-3 | OH | β-D-Glc-(1→6)-β-D-Glc | OH | OH | H | H |
| 39 | 133629-80-8 | OH | OH | OH | Glc | H | H |
| 40 | 133629-81-9 | OH | β-D-Glc | OH | β-D-Glc | H | H |
| 41 | 133629-82-0 | OH | Glc | OH | β-D-Glc-(1→6)-β-D-Glc | H | H |
| 42 | 133629-83-1 | OH | β-D-Glc-(1→6)-β-D-Glc | OH | β-D-Glc | H | H |
| 43 | 133629-84-2 | OH | β-D-Glc-(1→6)-β-D-Glc | OH | β-D-Glc-(1→6)-β-D-Glc | H | H |
| 44 | 19942-02-0 | OH | OH | OH | OH | H | OH |
| 45 | 23887-98-1 | OH | OH | OH | OH | H | H |
| 46 | 117773-94-1 | OH | OH | H | OH | H | H |
| 47 | 1447214-84-7 | OH | OH | OH | OH | H | α-OH |

-continued

| Entry | CAS # | R¹ (C-3) | R² (C-23) | R³ (C-16) | R⁴ (C-28) | R⁵ (C-22) | R⁶ (C-21) |
|---|---|---|---|---|---|---|---|
| 48 | 42483-24-9 | OH | OH | OH | OH | H | H |
| 49 | 1447214-87-0 | O= | OH | OH | OH | H | H |
| 50 | 1447214-89-2 | O= | OH | OH | OH | H | OH |
| 51 | 1447214-91-6 | O= | OH | OH | OH | OH | H |

(See Di Fabio et al., Molecules (2014) 19:10956-10981).

In certain embodiments, the gymnemic acid used in the lingual delivery forms and compositions of the present invention comprises one or more compounds of Formula (I) above. In other embodiments, the gymnemic acid comprises any one of or any combination of homologues of gymnemic acid, including but not limited to, GA 1 (Gymnemic Acid I), GA 2 (Gymnemic Acid II), GA 3 (Gymnemic Acid III), GA 4 (Gymnemic Acid IV), and GA 34 (Gymnemoside C).

The gymnemic acid used in the lingual delivery forms and compositions of the present invention can be of any purity, i.e., content of any combination of terpenoid saponins, where purity is defined as the proportion of gymnemic acid to the sum of gymnemic acid and other material from the *Gymnema sylvestre* plant. For example, the gymnemic acid used can have a purity of at least 20%, and least 30%, at least 40%, at least 50%, at least 55%, at least 60%, at least 65%, at least 70%, at least 75%, at least 80%, at least 85%, at least 90%, at least 90%, or at least 99%. In certain embodiments, the purity can be expressed in terms of either weight % or area % (AUC). Purity of the gymnemic acid may be determined by HPLC. In certain embodiments, purity may be determined using the USP <621> HPLC methodology. Preferably, HPLC is performed using a Waters XSelect CSH C18 Column, 130 Å, 5 μm, 4.6 mm×250 mm.

The gymnemic acid used in the lingual delivery forms and compositions of the present invention can be an inorganic salt, an ammonium salt, an amino salt including a polyamino salt, an organic salt, a cyclodextrin complex, a cryptand complex, a hydrate, or a solvate of gymnemic acid, or any combination thereof. Examples of inorganic salts of gymnemic acid include, but are not limited to, alkali metal salts, such sodium and potassium, alkaline earth metal salts, such as magnesium and calcium, transition metal salts, such as manganese, iron, and zinc, and rare earth metal salts, such as lanthanum, europium and terbium. Examples of ammonium salts of gymnemic acid include, but are not limited to, ammonium salts, mono-alkyl-substituted ammonium salts such as a methylammonium salt, di-alkyl-substituted ammonium salts, such as a dimethylammonium salt, tri-alkyl-substituted ammonium salt, such as a trimethylammonium salt, or tetra-alkyl-substituted ammonium salts, such as a tetramethylammonium salt. Examples of polyamino salts of gymnemic acid include, but are not limited to, are di-amino salts, such as an ethylenediamine salt, tri-amino salts, such as an diethylenetriamine salt, tetra-amino salts, such as a triethylenetetraamine salt, and other poly-amino salts, such as an α-polyornithine salt, an α-polylysine salt, a γ-polyornithine salt, an ε-polylysine salt, or a chitosan salt. Examples of cyclodextrin complexes of gymnemic acid include, but are not limited to, α-cyclodextrin, β-cyclodextrin, and γ-cyclodextrin complexes of gymnemic acid. Examples of solvates of gymnemic acid include ethanol solvates of gymnemic acid and ethyl acetate solvates of gymnemic acid. In certain embodiments, the gymnemic acid can be in the form of a protein salt with a protein having a pI of about 7 or more.

In certain embodiments of the present invention, the amino salt form of gymnemic acid can be a mono-alkyl substituted derivative of the amino salt form of gymnemic acid, a di-alkyl substituted derivative of the amino salt form of gymnemic acid, or a tri-alkyl substituted derivative of the amino salt form of gymnemic acid. In other embodiments of the present invention, the di-amino salt form of gymnemic acid can be a mono-alkyl substituted derivative of the di-amino salt form of gymnemic acid, a di-alkyl substituted derivative of the di-amino salt form of gymnemic acid, or a tri-alkyl substituted derivative of the di-amino salt form of gymnemic acid. In yet other embodiments of the present invention, the tri-amino salt form of gymnemic acid can be a mono-alkyl substituted derivative of the tri-amino salt form of gymnemic acid, a di-alkyl substituted derivative of the tri-amino salt form of gymnemic acid, or a tri-alkyl substituted derivative of the tri-amino salt form of gymnemic acid. In further embodiments of the present invention, the tetra-amino salt form of gymnemic acid can be a mono-alkyl substituted derivative of the tetra-amino salt form of gymnemic acid, a di-alkyl substituted derivative of the tetra-amino salt form of gymnemic acid, or a tri-alkyl substituted derivative of the tetra-amino salt form of gymnemic acid. In yet further embodiments of the present invention, the poly-amino salt form of gymnemic acid can be a mono-alkyl substituted derivative of the poly-amino salt form of gymnemic acid, a di-alkyl substituted derivative of the poly-amino salt form of gymnemic acid, or a tri-alkyl substituted derivative of the poly-amino salt form of gymnemic acid.

The gymnemic acid is present in any amount effective to partially or completely block the sensation of sweet taste in a subject for a period of time. Examples of such amounts include, but are not limited to, those in the range of about 0.01% to about 25% by weight, about 0.01% to about 10% by weight, about 0.01% to about 4% by weight, about 0.05% to about 2% by weight, about 0.01% to about 1% by weight, about 0.01% to about 0.5% by weight, and about 0.01% to about 0.2% by weight of the total weight of the lingual delivery form or composition. In certain embodiments, the gymnemic acid can be present in about 0.1% to 5% weight, 0.01 to 1% weight, about 0.01% to 0.5% weight, or about 0.01% to 0.2% weight of the lingual delivery form. In terms of absolute amount, the lingual delivery forms and compositions of the present invention may comprise about 0.1 mg to 200 mg of gymnemic acid, including but not limited to 1, 2, 3, 4, 5, 6, 7, 8, 9, 10, 15, 20, 25, 30, 35, 40, 45, 50, 55, 60, 65, 70, 75, 80, 85, 90, 95, 100, 150, or 200 mg of gymnemic acid. The amount of gymnemic acid in the lingual delivery forms and compositions of the present invention can vary depending on the composition and form of the composition (e.g., non-liquid or liquid). In this regard, the amount of gymnemic acid can be varied depending on the use and desired results. The remaining portion of the lingual delivery form can include other excipients including, but not limited to, sucrose, glucose, lactose, corn syrup solids, maltodextrin, sorbitol, xylitol, erythritol, and other carbohydrates and polyols. Furthermore, the lingual delivery form can include flavors such as peppermint, spearmint, and menthol.

Many flavors, such as vanilla and chocolate, also require the presence of sweet taste as a carrier, i.e., the flavor cannot be tasted unless the sweet taste is also present. However, mint does not require sweet taste as a carrier, and thus can be tasted and enjoyed without the presence of a sweet taste. Accordingly, the lingual delivery form may further comprise mint. For example, the mint may be peppermint, spearmint, or menthol. Moreover, while the addition of mint to gymnemic acid cannot block the bitter taste, to the extent there is any remaining bitterness upon administration of the lingual delivery form comprising gymnemic acid and a form of zinc, the mint will mask or block it.

In certain embodiments, the compositions of the present invention comprise gymnemic acid, a form of zinc, and at least one sour taste inhibitor. Any sour taste inhibitor known in the art may be used. An example of such a sour taste inhibitor includes, but is not limited to, miraculin.

The lingual delivery forms and the compositions of the present invention comprising gymnemic acid and a form of zinc may also further comprise at least one bitter taste inhibitor. Any bitter taste inhibitor known in the art may be used. Examples of such bitter taste inhibitors include, but are not limited to sodium salts.

The at least one bitter taste inhibitor, when included, is present in any amount effective to reduce or eliminate the bitter taste of the gymnemic acid. In certain embodiments, the bitter taste inhibitor is present in an amount in the range of from about 1 to about 200 mg. Specific examples of such amounts include, but are not limited to, about 1, 2, 3, 4, 5, 6, 7, 8, 9, 10, 15, 20, 25, 30, 35, 40, 45, 50, 55, 60, 65, 70, 75, 80, 85, 90, 95, 100, 150, or 200 mg of bitter taste inhibitor. For example, a form of zinc, such as a zinc salt may be present as a bitter taste inhibitor in an amount of, for example, 0.2%, 1%, 2%, or 5% by weight. In certain other embodiments, when the bitter taste inhibitor is a zinc salt, the percentage by weight of zinc ion is in the range of either 0.01% to 100%, or 1.0% to 75%, or 1.5% to 70%, or 2% to 65%, or 2.5% to 50%. The percentage weight of zinc ion is defined as the proportion of zinc ion to the sum of zinc ion plus gymnemic acid. Gymnemic acid content is determined according to the methods described above and zinc ion is determined according to zinc ion as percentage of the zinc form. For example, $Zn^{2+}$ is 40% of the molecular weight of zinc sulfate ($ZnSO_4$), therefore 10 mg of zinc sulfate is equivalent to 4 mg $Zn^{2+}$.

In certain embodiments, the combination of the gymnemic acid and form of zinc act synergistically in terms of the length of the resultant sweetness blockade. In certain embodiments, such synergistic combinations will result in the partial or complete inhibition of the sensation of sweet taste in a subject for about 30 minutes or more, about 60 minutes or more, about 90 minutes or more, or about 120 minutes or more. In certain embodiments, the combination of the gymnemic acid and form of zinc surprisingly act synergistically, prolonging the partial or complete sweetness blockade in a subject for periods longer than gymnemic acid administered to the oral cavity in the absence of at least one further sweet taste inhibitor and/or at least one sour taste inhibitor and/or at least one bitter taste inhibitor. Surprisingly, applicants found that the combination of the gymnemic acid (15 mg) and $ZnSO_4 \bullet 7H_2O$ (107 mg) resulted in complete blockade of sweet taste at 60 minutes following administration, where at 60 minutes partial recovery of sweet taste sensation had been found with administration of gymnemic acid alone.

In certain other embodiments, when the at least one further sweetness inhibitor is a zinc salt, the percentage by weight of zinc ion is in the range of either 0.01% to 100%, or 1.0% to 75%, or 1.5% to 70%, or 2% to 65%, or 2.5% to 50%. The percentage weight of zinc ion is defined as the proportion of zinc ion to the sum of zinc ion plus gymnemic acid, and where zinc ion and gymnemic acid content are determined according to the methods described above.

The methods of the present invention comprise administering the lingual delivery forms and compositions to a subject. In one embodiment, the method of administering the above lingual delivery forms and compositions to the subject results in a reduced appetite in the subject for sweet tasting foods and drinks. In another embodiment, the method of administering the above lingual delivery forms and compositions to the subject results in reduced calorie intake in the subject, since the subject no longer craves sweet tasting foods. In another embodiment, the method of administering the above lingual delivery forms and compositions to the subjects results in reduced dental caries in the subject, since the subject consumes less sweet tasting foods and drinks. In certain embodiments, the methods of the present invention include contacting (e.g., disposing, chewing, sucking, licking, or the like) an oral cavity of a subject with an amount of a lingual delivery form or composition. The oral cavity can include the tongue, inside of the mouth, the buccal cavity, under the tongue, and the like. In yet other embodiments, the composition is contacted with the oral cavity for a time period of about 1 to 10 minutes. In further embodiments, the composition can be contacted with the oral cavity multiple times, such as by chewing separate pieces of gum at various time frames during a time period (e.g., multiple hours, day, etc.).

In certain embodiments, the methods of the present invention provide for a sweetness blockade in the subject for a time period of about 30 to 120 minutes or about 60 minutes to 120 minutes upon contacting the composition with the oral cavity of the subject. In an embodiment, the time frame can start from the time the composition is no longer in the oral cavity, for example, when the gum is removed or the lozenge has undergone full dissolution.

This invention is further illustrated by the following examples, which should not be construed as limiting. The examples are set forth so as to provide those of ordinary skill in the art with an illustrative disclosure and description of how to perform the methods and use the compounds disclosed and claimed herein. Those skilled in the art will recognize that the invention may be practiced with variations on the disclosed structures, materials, compositions and methods, and such variations are regarded as within the ambit of the invention. Unless indicated otherwise, parts are parts by weight, temperature is in ° C., and pressure is at or near atmospheric. Standard temperature and pressure are defined as 20° C. and 1 atmosphere.

EXAMPLES

Formulation Examples

Formulation FLLC-F27c 4 mg (Extended Release Formulation)

| Excipient Name | % Ratio | Weight (grams) | 40X grams | 100X grams | 240X grams |
| --- | --- | --- | --- | --- | --- |
| Active (Four-cc1-15B) [gymnemic acid] | 0.800 | 0.0040 | 0.160 | 0.400 | 0.960 |

-continued

| Excipient Name | % Ratio | Weight (grams) | 40X grams | 100X grams | 240X grams |
|---|---|---|---|---|---|
| Sorbitol (Parateck S1 150) | 62.100 | 0.3105 | 12.420 | 31.050 | 74.520 |
| Erythritol | 30.000 | 0.1500 | 6.000 | 15.000 | 36.000 |
| Zinc Gluconate | 1.300 | 0.0065 | 0.260 | 0.650 | 1.560 |
| Ferminich Peppermint | 2.400 | 0.0120 | 0.480 | 1.200 | 2.880 |
| Ferminich Mint | 2.400 | 0.0120 | 0.480 | 1.200 | 2.880 |
| Magnesium Stearate | 1.000 | 0.0050 | 0.200 | 0.500 | 1.200 |
| Total | 100.000 | 0.5000 | 20.000 | 50.000 | 120.000 |

Comments

Used a 10 mm Concave die to make a 500 mg tablet.
Formulation Procedure Used:
Co-milled the active with 1 gram of Erythritol and Zinc Gluconate to a fine homogenous powder Sieved remaining excipients through 30 mesh screen. Then combined all excipients except for magnesium stearate.
Blended for 30 minutes
Added magnesium stearate
Blended for 1 minute
Pressed formulation into tablets
Taste Blocking Examples A standard method was developed to quantify the duration of sweet taste blockade for the gymnemic acid compositions of the present invention. The gymnemic acid used in the following examples was partially purified from a crude extract of *Gymnema sylvestre* leaves and was determined to be a mixture of gymnemic acids (81% purity), which was primarily GA 1 and GA 2, with lesser amounts of GA 3 and GA 4 and also including a GA acetate/benzoate diester (i.e., GA 34-Gymnemoside C). In all cases, sucrose was used as the sweetener in sweet taste blockade quantification. Thus, 10%, 8%, 6%, 4%, and 2% (w/v) sucrose solutions in reverse osmosis (RO) purified water were freshly prepared and, at the beginning of each experiment, 15 mL samples of each sucrose solution were used to calibrate sensory panelist on sweetness intensity. The sensory panelist is described as a person with training in sensory evaluation with at least 1 year of experience as a sensory panelist in the area of gustatation, and preferably with training in descriptive analysis. Standard scaling methodology was used for quantification of sweetness intensity (SI) on the following scale:

10% sucrose=10,
8% sucrose=8,
6% sucrose=6,
4% sucrose=4,
2% sucrose=2, and
0% sucrose=0.

Following panelist calibration with the sucrose reference standards, the panelist rinsed their mouth with 15 mL RO water and the sweetness inhibitor sample in 15 mL RO water was then immediately taken into the mouth and gently agitated for 5 minutes. The sweet taste inhibitor sample was then expectorated and a 15 mL sample of the 10% sucrose reference solution was then immediately re-tasted, perceived SI within 15 seconds was rated on the 0-10 scale, the sample expectorated, and the mouth rinsed vigorously with 15 mL RO water. The 10% sucrose sample was then re-tasted every 15 min and SI rated. The panelist was asked to make comments on the observations of non-sweet taste attributes at each sucrose reference tasting interval. SI results in experiments by this standard protocol are simple means of the SI ratings.

Gymnemic acid exhibits significant bitter off-taste. Scaling methodology was employed to quantify the bitterness of gymnemic acid alone and in combination with a variety of substances in effort to identify gymnemic acid compositions with diminished or eliminated bitter taste. In this methodology, sucrose was used as the scaling reference. Thus, as above, bitterness ratings of 10, 8, 6, 4, 2, and 0 are indicative of perceptions of bitter taste equivalent in intensity to sweet taste perceptions of 10, 8, 6, 4, 2, and 0% sucrose, respectively.

Comparative Example 1

Sweetness Inhibition of Gymnemic Acid (15 mg Dosage)

Gymnemic acid was evaluated to quantify the duration of its sweet taste inhibition in order to determine a baseline value against which to compare the following inventive examples. Results obtained are summarized in Table 1.

TABLE 1

| Time (min) | SI | Comments & Observations |
|---|---|---|
| 0 | 0 | No sweetness; strong bitterness. |
| 15 | 0 | No sweetness; medium bitterness. |
| 30 | 0 | No sweetness; weak/medium bitterness. |
| 45 | 1 | Faint sweetness; weak bitterness. |
| 60 | 1 | Faint sweetness; faint bitterness. |
| 75 | 2 | Weak sweetness; no bitterness. |
| 90 | 3 | Weak sweetness; no bitterness. |
| 105 | 7 | Medium to strong sweetness; no bitterness. |
| 120 | 10 | Strong sweetness; no bitterness. |

Comparative Example 2

Sweetness Inhibition of Lactisole (3 mg Dosage)

Lactisole was evaluated to quantify the duration of its sweet taste inhibition in order to determine its potential value in combination with gymnemic acid. Lactisole differs from gymnemic acid as a sweetness blocker, for example, the sweetness blockade provided by lactisole does not linger after exposure to the tongue. However, surprisingly, it was observed that following exposure of the oral cavity to lactisole, no sweet taste inhibition was observed, not even when the 10% sucrose reference was tasted immediately after lactisole expectoration.
Results obtained are summarized in Table 2.

TABLE 2

| Time (min) | SI | Comments & Observations |
|---|---|---|
| 0 | 12 | Very strong sweetness greater than 10% sucrose reference; no bitterness. |
| 15 | 10 | Strong sweetness; no bitterness. |
| 30 | 10 | Strong sweetness; no bitterness. |
| 45 | 10 | Strong sweetness; no bitterness. |
| 60 | 10 | Strong sweetness; no bitterness. |
| 75 | 10 | Strong sweetness; no bitterness. |
| 90 | 10 | Strong sweetness; no bitterness. |
| 105 | 10 | Strong sweetness; no bitterness. |
| 120 | 10 | Strong sweetness; no bitterness. |

Example 1

Sweetness Inhibition of Blend of Gymnemic Acid (15 mg) and Lactisole (3 mg)

A gymnemic acid/lactisole blend was evaluated to quantify the duration of its sweet taste inhibition. Results obtained are summarized in Table 3.

TABLE 3

| Time (min) | SI | Comments & Observations |
|---|---|---|
| 0 | 3 | Weak sweetness; strong bitterness. |
| 15 | 2 | Weak sweetness; strong bitterness. |
| 30 | 2 | Faint sweetness; strong bitterness. |
| 45 | 1 | Faint sweetness; strong bitterness. |
| 60 | 1 | Faint sweetness; medium/strong bitterness. |
| 75 | 1 | Faint sweetness; medium/strong bitterness. |
| 90 | 2 | Weak sweetness; medium bitterness. |
| 105 | 4 | Weak/medium sweetness; medium bitterness. |
| 120 | 5 | Medium sweetness; medium bitterness. |

Surprisingly, when the 10% sucrose reference sample was tasted immediately following oral cavity treatment with the gymnemic acid/lactisole blend, it was observed to have weak to moderate intensity sweet taste and not tasteless, as when pre-treatment was carried out with gymnemic acid alone. This initial sweetness is of significant benefit for improvement of the overall sensorial experience of a sweet taste inhibitory composition and is not possible with gymnemic acid or other gymnemic acid formulations. Also, surprisingly, it was observed that while lactisole itself caused no sweetness inhibition following expectoration, the gymnemic acid/lactisole blend caused a prolonged duration of sweet taste inhibition relative to the duration of sweet taste inhibition with gymnemic acid alone. Thus, though the biochemical mechanism is not clear, it is apparent that lactisole in combination with gymnemic acid results in a synergistic sweet taste inhibitory effect, one where weak sweet taste is observed in the first 30 minutes following gymnemic acid/lactisole pre-treatment. This effect may be of value to improve the overall sensory experience of sweet taste inhibitory products formulated to provide prolonged blockade of sweetness.

Comparative Example 3

Sweetness Inhibition of Zinc Sulfate Heptahydrate ($ZnSO_4 \cdot 7H_2O$, 107 mg Dosage)

$ZnSO_4 \cdot 7H_2O$ was evaluated to quantify the duration of its sweet taste inhibition in order to determine its potential value in combination with gymnemic acid. Surprisingly, it was observed that $ZnSO_4 \cdot 7H_2O$, like gymnemic acid, does cause a prolonged period of sweet taste inhibition, though not nearly as prolonged as is the case with gymnemic acid, as sweetness sensitivity was 100% restored after 60 minutes. Results obtained are summarized in Table 4.

TABLE 4

| Time (min) | SI | Comments & Observations |
|---|---|---|
| 0 | 0 | No sweetness or bitterness; weak astringency. |
| 15 | 2 | Weak sweetness; no bitterness; weak astringency. |
| 30 | 5 | Medium sweetness; no bitterness; faint astringency. |
| 45 | 8 | Strong sweetness; no bitterness; faint astringency. |
| 60 | 10 | Strong sweetness; no bitterness or astringency. |
| 75 | 10 | Strong sweetness; no bitterness or astringency. |
| 90 | 10 | Strong sweetness; no bitterness or astringency. |
| 105 | 10 | Strong sweetness; no bitterness or astringency. |
| 120 | 10 | Strong sweetness; no bitterness or astringency. |

Example 2

Sweetness Inhibition of Blend of Gymnemic Acid (15 mg) and $ZnSO_4 \cdot 7H_2O$ (107 mg)

A blend of gymnemic acid/$ZnSO_4 \cdot 7H_2O$ was then evaluated for duration of sweet taste blockade. Results are summarized in Table 5.

TABLE 5

| Time (min) | SI | Comments & Observations |
|---|---|---|
| 0 | 0 | No sweetness or bitterness; weak astringency. |
| 15 | 0 | No sweetness or bitterness; faint astringency. |
| 30 | 0 | No sweetness or bitterness; faint astringency. |
| 45 | 0 | No sweetness or bitterness; faint astringency. |
| 60 | 0 | No sweetness or bitterness; faint astringency. |
| 75 | 1 | Faint sweetness; no bitterness or astringency. |
| 90 | 2 | Faint sweetness; no bitterness or astringency. |
| 105 | 3 | Weak sweetness; no bitterness or astringency. |
| 120 | 4 | Medium sweetness; no bitterness or astringency. |

Surprisingly, complete blockade of sweet taste was still observed at 60 minutes while partial recovery occurs by that time when gymnemic acid is used alone. Thus, although the mechanistic process is unclear, the combination of $ZnSO_4 \cdot 7H_2O$ with gymnemic acid clearly possesses a synergistic sweet taste inhibitory effect.

Comparative Example 4

Sweetness Inhibition of Miraculin (80 mg Dosage)

Miraculin was evaluated to quantify the duration of its sweet taste inhibition in order to determine its potential value in combination with gymnemic acid. No sweet taste inhibitory effect was observed following miraculin pre-treatment of the oral cavity. Results obtained are summarized in Table 6.

TABLE 6

| Time (min) | SI | Comments & Observations |
|---|---|---|
| 0 | 10 | Strong sweetness and no other taste. |
| 15 | 10 | Strong sweetness and no other taste. |
| 30 | 10 | Strong sweetness and no other taste. |
| 45 | 10 | Strong sweetness and no other taste. |
| 60 | 10 | Strong sweetness and no other taste. |
| 75 | 10 | Strong sweetness and no other taste. |
| 90 | 10 | Strong sweetness and no other taste. |
| 105 | 10 | Strong sweetness and no other taste. |
| 120 | 10 | Strong sweetness and no other taste. |

Example 3

Sweetness Inhibition of Blend of Gymnemic Acid (15 mg) and Miraculin (80 mg)

Even though no sweet taste inhibitory effect was observed, miraculin was nonetheless evaluated in combination with gymnemic acid to determine if any prolongation of gymnemic acid sweet taste inhibition duration would be observed. It was observed that miraculin did prolong the duration of gymnemic acid sweet taste blockade. As such, miraculin in combination with gymnemic acid results in a synergistic inhibitory effect on sweet taste. Results are summarized in Table 7.

TABLE 7

| Time (min) | SI | Comments & Observations |
|---|---|---|
| 0 | 0 | No sweetness; weak bitterness and some sourness. |
| 15 | 0 | No sweetness; weak bitterness. |
| 30 | 0 | No sweetness and no bitterness. |
| 45 | 0 | No sweetness and no bitterness. |
| 60 | 1 | Very faint sweetness, just above threshold and no other taste. |
| 75 | 1 | Very faint sweetness, just above threshold and no other taste. |
| 90 | 2 | Weak sweetness and no other taste. |
| 105 | 3 | Weak sweetness and no other taste. |
| 120 | 5 | Medium sweetness; no bitterness. |

Example 4

Sweetness Inhibition of Blend of Gymnemic Acid (15 mg), Lactisole (3 mg), and $ZnSO_4 \cdot 7H_2O$ (107 mg)

As demonstrated above, lactisole and $ZnSO_4 \cdot 7H_2O$, when used independently in combination with gymnemic acid, exhibit synergy in sweetness inhibition. A ternary blend composition containing both of these sweet taste inhibitors in combination with gymnemic acid was evaluated to determine if increased synergy would be present. Results are summarized in Table 8.

TABLE 8

| Time (min) | SI | Comments & Observations |
|---|---|---|
| 0 | 0 | No sweetness or bitterness at all; only medium/strong astringency. |
| 15 | 0 | No sweetness or bitterness at all; only medium/strong astringency. |
| 30 | 0 | No sweetness or bitterness at all; only medium astringency. |
| 45 | 1 | Very faint sweetness; no bitterness; only weak/medium astringency. |
| 60 | 1 | Very faint sweetness; no bitterness; only weak/medium astringency. |
| 75 | 2 | Weak sweetness; no bitterness; only weak/medium astringency. |
| 90 | 2 | Weak sweetness; no bitterness; only weak astringency. |
| 105 | 3 | Weak sweetness, but slightly > than @ 90 min; no bitterness; only weak astringency. |
| 120 | 4 | Weak/medium sweetness slightly > than @ 105 min; no bitterness and weak astringency. |

A comparison of the sweet taste inhibition results of this ternary blend with the results of Examples 1 and 2 show that increased synergy is not observed. However, this ternary blend formulation is clearly advantageous in that the synergies present in the gymnemic acid binary blends with lactisole and $ZnSO_4 \cdot 7H_2O$ remain, while full inhibition of the bitter off-taste of gymnemic acid is realized.

Gymnemic acid, when used in aqueous compositions or formulated in lozenges or tablets, exhibits weak to medium or even strong bitter off-tastes, which is a limitation to its effective use in formulations designed to aid consumers in controlling their intake of caloric sweet products.

Comparative Example 5

Bitterness of Gymnemic Acid (15 mg Dosage)

A solution of 15 mg gymnemic acid in 15 mL RO water was evaluated and found to have a bitterness score of 10 on a 15-point scale for bitterness.

Example 5

Bitterness of Blend of Gymnemic Acid (15 mg) and $ZnSO_4 \cdot 7H_2O$ (107 mg)

A solution of 15 mg gymnemic acid in 10 mL RO water was combined with a solution of 107 mg $ZnSO_4 \cdot 7H_2O$ in 5 mL RO water and evaluated. It was found to have a bitterness score of 0. Aqueous solutions containing 60, 34, 19, 10.7, 6 and 3.4 mg, respectively, of $ZnSO_4 \cdot 7H_2O$ in 5 mL RO water were combined with 15 mg gymnemic acid in 10 mL RO water samples. The resultant mixtures exhibited bitterness intensities of 0, 0, 0, 1, 4 and 7, respectively. Thus, these gymnemic acid/$ZnSO_4 \cdot 7H_2O$ compositions exhibit an absence of bitterness when the $ZnSO_4 \cdot 7H_2O$ concentrations are equal to or greater than approximately 0.6 mg/mL (2 mM).

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure.

The invention claimed is:

1. An orally disintegrating tablet having a disintegration time in the range of from about 30 seconds to about 5 minutes, comprising at least one form of gymnemic acid and at least one form of zinc, wherein the tablet is palatable when delivered to the oral cavity.

2. A composition comprising at least one form of gymnemic acid and zinc gluconate, wherein the composition is palatable when delivered to the oral cavity.

3. A composition comprising at least one form of gymnemic acid and at least one form of zinc, wherein the composition is palatable when delivered to the oral cavity, and wherein the at least one form of gymnemic acid is selected from the group consisting of an inorganic salt of gymnemic acid, an organic salt of gymnemic acid, a cyclodextrin complex of gymnemic acid, a cryptand complex of gymnemic acid, a hydrate of gymnemic acid, a solvate of gymnemic acid, and combinations thereof.

4. The composition of claim 3, wherein the solvate of gymnemic acid is selected from the group consisting of ethanol solvates of gymnemic acid and combinations thereof.

5. A composition comprising at least one form of gymnemic acid, at least one form of zinc, and mint, wherein the composition is palatable when delivered to the oral cavity.

6. A composition comprising at least one form of gymnemic acid, at least one form of zinc, and a bitter taste inhibitor which is selected from the group consisting of a sodium salt, a lipoprotein, and combinations thereof, wherein the composition is palatable when delivered to the oral cavity.

7. A composition comprising at least one form of gymnemic acid, at least one form of zinc, and at least one sour taste inhibitor, wherein the composition is palatable when delivered to the oral cavity.

8. The composition of claim 7, wherein the at least one sour taste inhibitor is miraculin.

9. A lingual delivery form comprising at least one form of gymnemic acid and at least one form of zinc, wherein the delivery form is palatable when delivered to the oral cavity.

10. The lingual delivery form of claim 9, wherein the delivery form is selected from the group consisting of a lozenge, an orally disintegrating tablet, an orally dispersible tablet, a troche, a hard candy, a soft candy, a jelly, a gum, an edible film, an orally dissolvable film, a wafer, a drop, an oral spray, a liquid, a powder and combinations thereof.

11. The lingual delivery form of claim 10, wherein the delivery form is an orally disintegrating tablet having a disintegration time in the range of from about 30 seconds to about 5 minutes.

12. The lingual delivery form of claim 9, wherein the at least one form of zinc is selected from the group consisting of zinc acetate, zinc carbonate, zinc chloride, zinc citrate, zinc gluconate, zinc sulfate, zinc hydrosulfite, zinc bisulfate, zinc oxide, zinc halide, zinc hydride, zinc carbide, and combinations thereof.

13. The lingual delivery form of claim 9, wherein the at least one form of zinc is zinc gluconate.

14. The lingual delivery form of claim 9, wherein the at least one form of gymnemic acid is selected from the group consisting of an inorganic salt of gymnemic acid, an organic salt of gymnemic acid, a cyclodextrin complex of gymnemic acid, a cryptand complex of gymnemic acid, a hydrate of gymnemic acid, a solvate of gymnemic acid, and combinations thereof.

15. The lingual delivery form of claim 14, wherein the solvate of gymnemic acid is selected from the group consisting of ethanol solvates of gymnemic acid and combinations thereof.

16. The lingual delivery form of claim 9, further comprising mint.

17. The lingual delivery form of claim 9, further comprising a bitter taste inhibitor which is selected from the group consisting of a sodium salt, a lipoprotein, and combinations thereof.

18. The lingual delivery form of claim 9, further comprising at least one sour taste inhibitor.

19. The lingual delivery form of claim 18, wherein the at least one sour taste inhibitor is miraculin.

20. A method of reducing sugar consumption, comprising administering to a subject a composition comprising at least one form of gymnemic acid and at least one form of zinc, wherein the composition is palatable when delivered to the oral cavity.

21. A method of reducing calorie intake, comprising administering to a subject a composition comprising at least one form of gymnemic acid and at least one form of zinc, wherein the composition is palatable when delivered to the oral cavity.

22. A method of reducing dental caries, comprising administering to a subject a composition comprising at least one form of gymnemic acid and at least one form of zinc, wherein the composition is palatable when delivered to the oral cavity.

* * * * *